United States Patent [19]
Ritchart et al.

[11] Patent Number: 5,810,806
[45] Date of Patent: Sep. 22, 1998

[54] METHODS AND DEVICES FOR COLLECTION OF SOFT TISSUE

[75] Inventors: Mark A. Ritchart, Murrieta; Minh Tran, Westminster; Mark Cole, Santa Ana; Fred H. Burbank, San Juan Capistrano, all of Calif.

[73] Assignee: Ethicon Endo-Surgery, Cincinnati, Ohio

[21] Appl. No.: 705,622

[22] Filed: Aug. 29, 1996

[51] Int. Cl.$^6$ ............................................. A61B 17/39
[52] U.S. Cl. ........................ 606/45; 606/46; 606/41; 604/21
[58] Field of Search .................. 606/41, 42, 45–50; 604/21, 22

[56] References Cited

U.S. PATENT DOCUMENTS

| | | | |
|---|---|---|---|
| 3,850,162 | 11/1974 | Iglesias | 606/46 |
| 4,362,160 | 12/1982 | Hiltebrandt | 606/46 |
| 4,782,840 | 11/1988 | Martin, Jr. et al. . | |
| 4,801,803 | 1/1989 | Denen et al. . | |
| 4,889,991 | 12/1989 | Ramsey et al. . | |
| 4,893,013 | 1/1990 | Denen et al. . | |
| 4,959,547 | 9/1990 | Carroll et al. . | |
| 5,014,708 | 5/1991 | Hayashi et al. | 606/46 |
| 5,036,201 | 7/1991 | Carroll et al. . | |
| 5,047,027 | 9/1991 | Rydell | 606/48 |
| 5,064,424 | 11/1991 | Bitrolf | 606/46 |
| 5,070,878 | 12/1991 | Denen . | |
| 5,111,828 | 5/1992 | Konberg et al. . | |
| 5,119,818 | 6/1992 | Carroll et al. . | |
| 5,148,040 | 9/1992 | Wise, Jr. et al. . | |
| 5,151,598 | 9/1992 | Denen . | |
| 5,170,055 | 12/1992 | Carroll et al. . | |
| 5,201,731 | 4/1993 | Hakky | 606/15 |
| 5,221,281 | 6/1993 | Klicek . | |
| 5,246,005 | 9/1993 | Carroll et al. . | |
| 5,304,176 | 4/1994 | Phillips | 606/41 |
| 5,312,327 | 5/1994 | Bales et al. | 606/46 |
| 5,348,555 | 9/1994 | Zinnanti | 606/49 |
| 5,383,456 | 1/1995 | Arnold et al. . | |
| 5,395,312 | 3/1995 | Desai | 606/45 |
| 5,400,564 | 3/1995 | Humphries et al. . | |
| 5,403,311 | 4/1995 | Abele et al. | 606/49 |
| 5,429,133 | 7/1995 | Thurston et al. . | |
| 5,441,050 | 8/1995 | Thurston et al. . | |
| 5,441,503 | 8/1995 | Considine et al. | 606/46 |
| 5,456,689 | 10/1995 | Kresch et al. . | |
| 5,475,219 | 12/1995 | Olson . | |
| 5,495,111 | 2/1996 | Thurston et al. . | |
| 5,526,822 | 6/1996 | Burbank et al. . | |
| 5,527,331 | 6/1996 | Kresch et al. . | |
| 5,575,293 | 11/1996 | Miller et al. . | |

OTHER PUBLICATIONS

Surgical resection and radiolocalization of the sentinel lymph node in breast cancer using a gamma probe; Krag et a. — Surgical Oncology 1993; 2; 335–340.

"Techniques of laparoscopic morcellation of the spleen" M.J. Legrand et al.; Minimally Invasive Therapy & Applied Technology 1996: vol. 5: No. 2; pp. 143–146.

*Primary Examiner*—Michael Peffley

[57] ABSTRACT

This invention provides an inventive tissue sampling probe which offers many advantages over probes available in the prior art. Unexpectedly superior results are obtained in connection with the retrieval of intact tissue specimens, because of a unique combination of cutting features, including, for example, the employment of an electrosurgical cutting element and a vacuum assist in one preferred embodiment. A particularly important feature of the invention is the ability to manipulate the electrosurgical cutting element to cleanly sever the distal end of the tissue specimen. In certain embodiments, this is accomplished without any cutting impact on surrounding tissue. The versatility of the invention permits its use in many applications, including, for example, breast biopsies, laparoscopic surgery, and lymphadenectomy procedures.

40 Claims, 12 Drawing Sheets

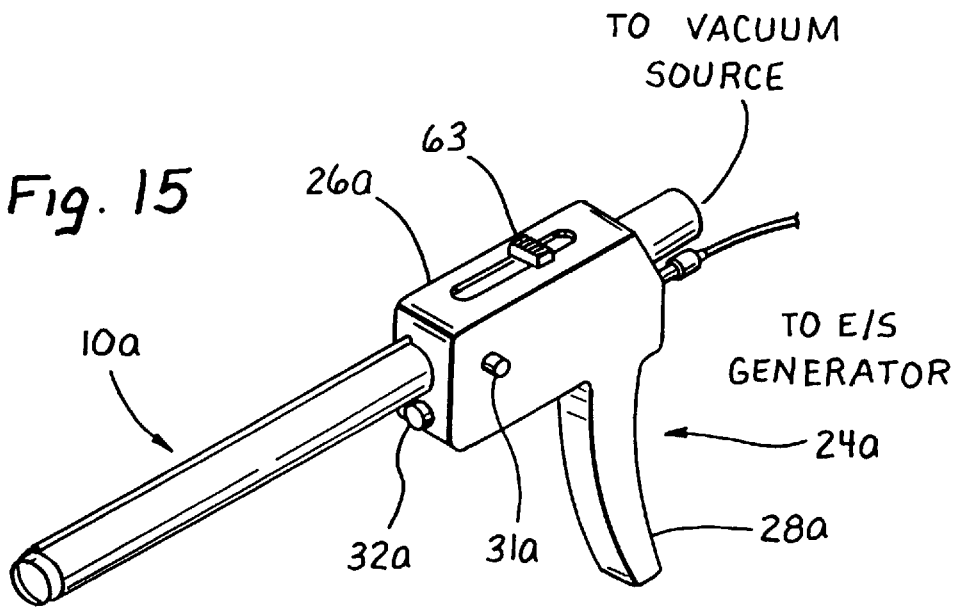
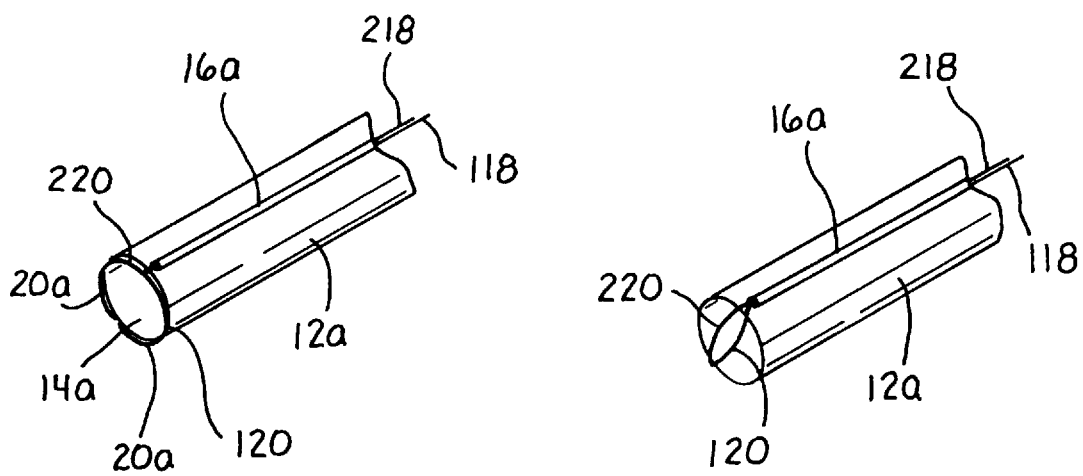

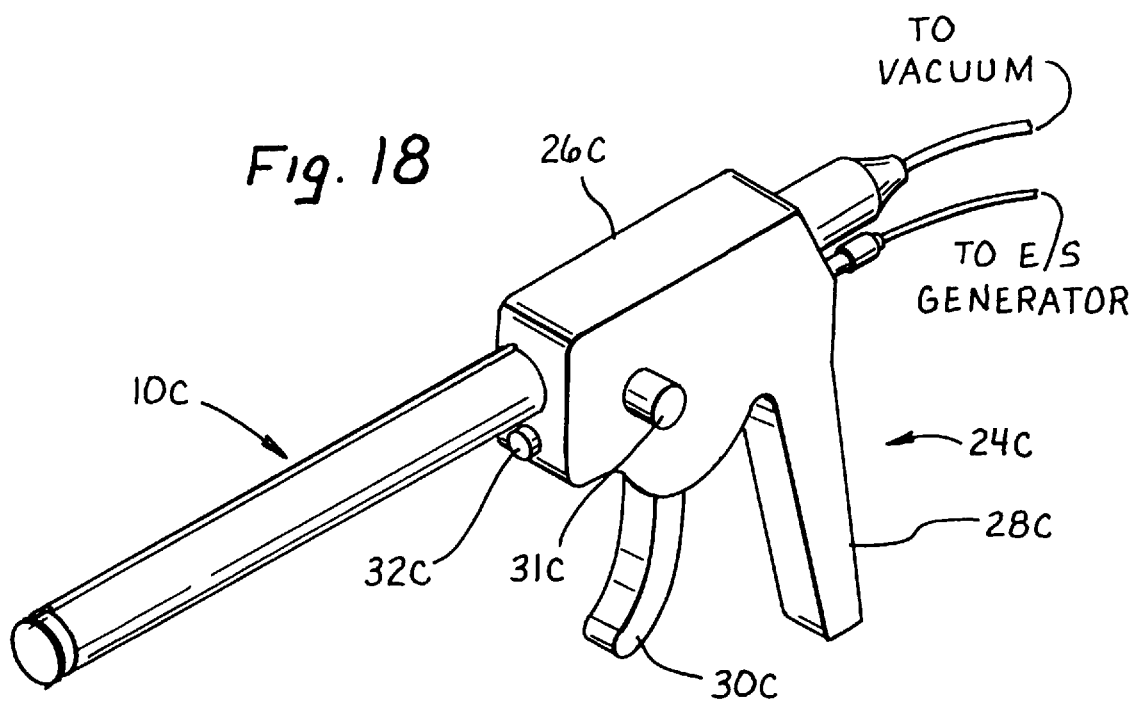
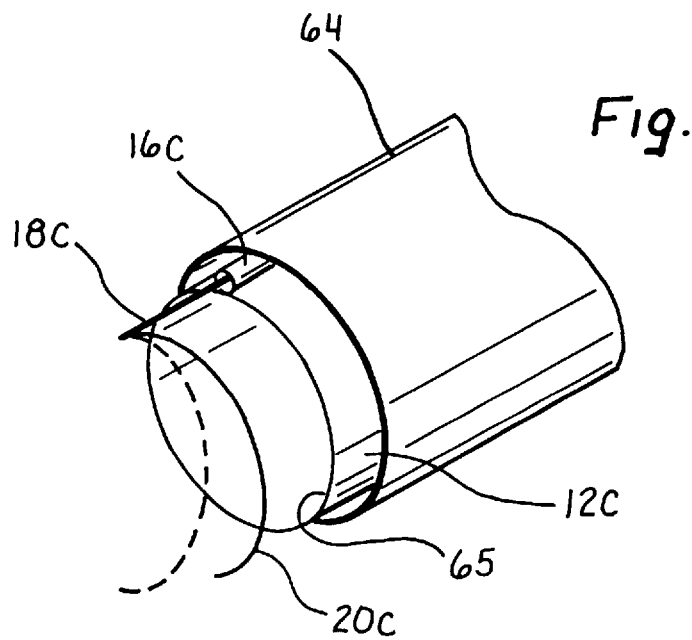

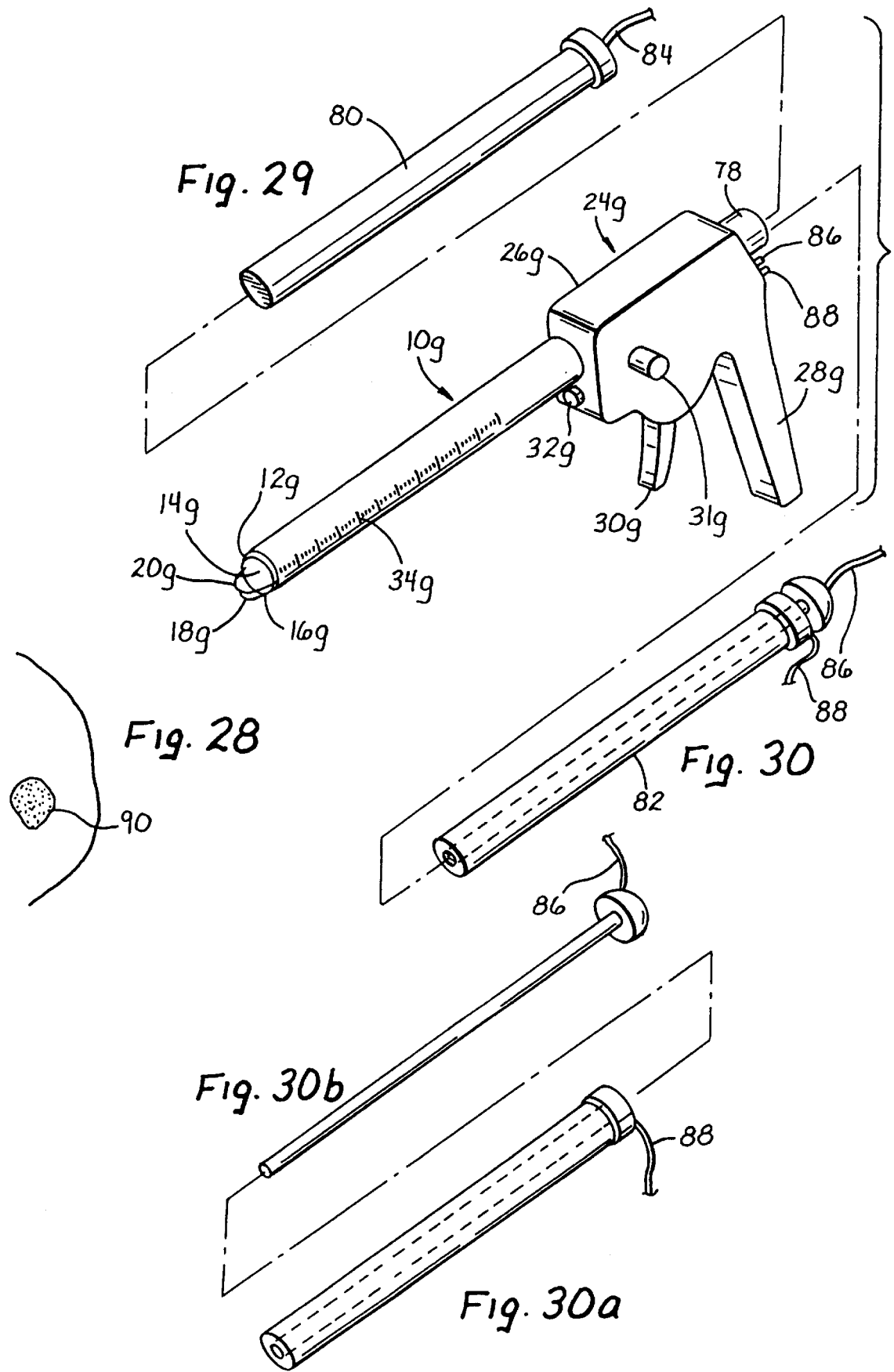

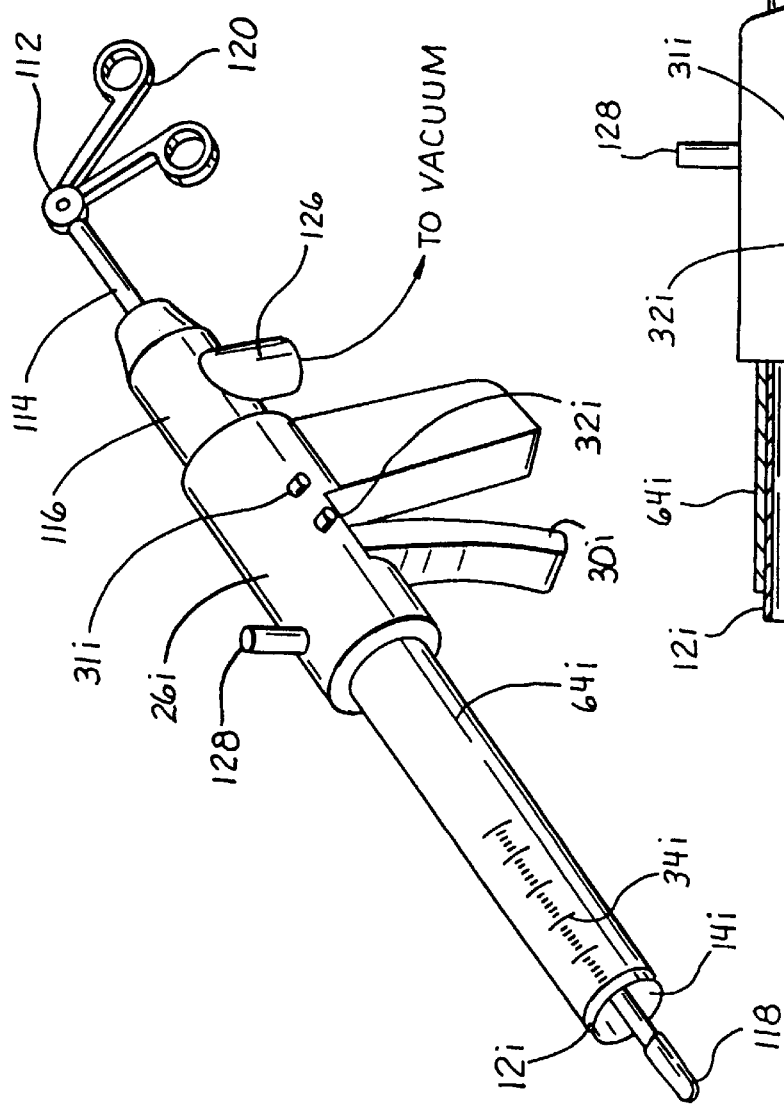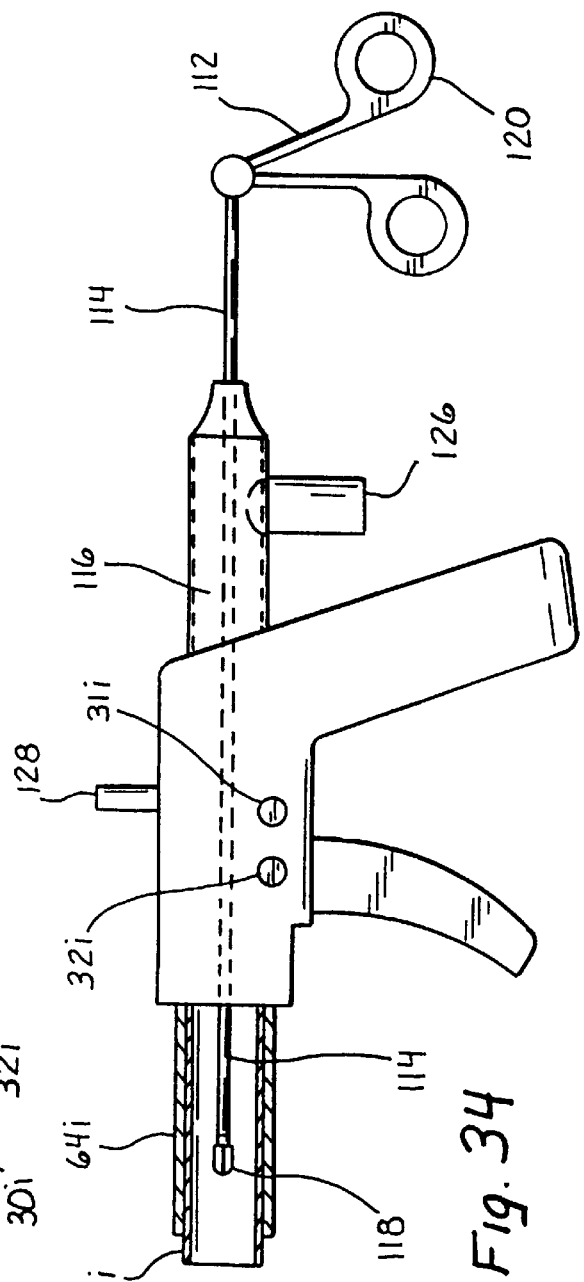

METHODS AND DEVICES FOR COLLECTION OF SOFT TISSUE

FIELD OF THE INVENTION

The present invention relates to methods and devices for tissue sampling, and more specifically to improved instruments and methods for acquiring soft body tissue.

BACKGROUND OF THE INVENTION

It is often desirable and frequently necessary to sample or test a portion of tissue from humans and other animals, particularly in the diagnosis and treatment of patients with cancerous tumors, pre-malignant conditions, and other diseases or disorders.

Typically, in the case of breast cancer, there is a great emphasis on early detection and diagnosis through the use of screening modalities, such as physical examination, and particularly mammography, which is capable of detecting very small abnormalities, often nonpalpable. When the physician establishes by means of a mammogram or other screening modality that suspicious circumstances exist, a biopsy must be performed to capture tissue for a definitive diagnosis as to whether the suspicious lesion is cancerous. Biopsy may be done by an open or percutaneous technique. Open biopsy, which is an invasive surgical procedure using a scalpel and involving direct vision of the target area, removes the entire mass (excisional biopsy) or a part of the mass (incisional biopsy). Percutaneous biopsy, on the other hand, is usually done with a needle-like instrument through a relatively small incision, blindly or with the aid of an artificial imaging device, and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section.

The type of biopsy utilized depends in large part on circumstances present with respect to the patient, including the location of the lesion(s) within the body, and no single procedure is ideal for all cases. However, core biopsy is extremely useful in a number of conditions and is being used more frequently by the medical profession.

A very successful type of image guided percutaneous core breast biopsy instrument currently available is a vacuum-assisted automatic core biopsy device. One such successful biopsy device is shown and disclosed in U.S. Pat. No. 5,526,822, U.S. patent application Ser. No. 08/386,941, filed on Feb. 10, 1995, and U.S. patent application Ser. No. 08/568,143, filed on Dec. 6, 1995, all of which are commonly owned by the assignee of the present application and are herein incorporated by reference. This device, known commercially as the MAMMOTOME® Biopsy System, has the capability to active capture tissue prior to cutting the tissue. Active capture allows for sampling through non-homogeneous tissues, meaning that the device is equally capable of cutting through hard and soft tissue. The device is comprised of a disposable probe, a motorized drive unit, and an integrated vacuum source. The probe is made of stainless steel and molded plastic and is designed for collection of multiple tissue samples with a single insertion of the probe into the breast. The tip of the probe is configured with a laterally disposed sampling notch for capturing tissue samples. Orientation of the sample notch is directed by the physician, who uses a thumbwheel to direct tissue sampling in any direction about the circumference of the probe. A hollow cylindrical cutter severs and transports tissue samples to a tissue collection chamber for later testing.

While the MAMMOTOME Biopsy System functions very well as a core biopsy device, there are occasions when because of the size of a lesion, or its location, it may be advantageous to use a core biopsy device of a type disclosed in U.S. Pat. No. 5,111,828, to Kornberg et al., also expressly incorporated by reference herein, wherein the tissue receiving port is disposed at the distal end of the device and is oriented axially rather than laterally. A disadvantage of this type of device, however, is the lack of ability to effectively and efficiently draw tissue into the receiving chamber prior to and during the tissue cutting process. A second disadvantage is the requirement to withdraw the device from parent tissue and remove the first specimen, reassemble the device, then reintroduce the device for each desired specimen A third disadvantage is the necessity of manually handling each specimen obtained.

On other occasions, the ability to sample any selected area of a cavity wall from within the cavity may be important, which ability requires the use of a flexible probe.

Furthermore, it is desirable during the biopsy process to "stage" the spread of a cancer. For example, breast cancer starts in the milk ducts, the mammary glands. The initial change towards breast cancer is now thought to be the development of atypical ductal hyperplasia. The next step is thought to be represented by ductal carcinoma in situ. Finally, the last step in the development of breast cancer is infiltrating ductal carcinoma. By the time the breast cancer has reached the stage of infiltrative ductal carcinoma, breast cancer cells have developed the ability to migrate from the duct of origin, disassociate themselves from one another, and enter vascular structures, such as the lymphatic channels. When these malignant infiltrative ductal carcinoma cells enter the vascular system, they can spread or metastasize to other parts of the body. It is this metastatic process that ultimately leads to death from breast cancer.

When breast cancer cells enter the lymphatic system, they metastasize in an orderly fashion to regional lymph nodes. Drainage can occur to the axillary lymph nodes, the supraclavicular lymph nodes, the lateral thoracic lymph nodes, and to the internal mammary lymph nodes.

It is the current standard of practice to determine if breast cancer cells have extended to regional lymph nodes by surgically performing an axillary lymph node dissection known as lymphadenectomy. In this open surgical procedure, a relatively large incision (5–10 cm), is made at the axilla (the armpit). Through this incision, a relatively large volume (15 to 30 grams) of fatty tissue and lymph node tissue are removed.

During this process, anywhere from 10 to 30 lymph nodes can be recovered and submitted to pathology, where each of these lymph nodes is examined for the presence or absence of metastatic breast cancer. Based on positive lymph node findings, systemic therapy will be given to the patient with breast cancer, including chemotherapy. If, on the other hand, the lymph nodes of the axilla are free of metastatic disease, then the use of systemic therapies is limited.

Surgical lymphadenectomy carries a low mortality, but high morbidity. The most common morbidity is the development of lymph edema in the arm, which is ipsilateral to the axilla dissected. The development of lymph edema in the ipsilateral arm is, at times, a debilitating complication.

It has been shown in the examination of lymphatic drainage of melanoma, and now shown in the lymphatic drainage of breast cancers, that lymphatic drainage patterns can be defined by the injection of a radioisotope (or other traceable marker such as blue dye) into the bed of the tumor. The isotope (or dye) is then followed, either visually, with a gamma camera imaging system, or with a Geiger counter-type of counting system.

The spread of cancer cells is orderly, the first lymph node reached by the drainage channels from the infected breast containing the most cancer cells. Consequently, the first lymph node in the draining system is referred to as the "sentinel" lymph node.

It has been further shown, if one simply removes the sentinel lymph node, the determination of whether or not breast cancer has metastasized to the regional lymph nodes of the axilla can be established without excision of the remaining lymph nodes in the axilla. The surgical removal of only one lymph node greatly reduces the complications of lymph node surgery including the morbidity of lymph edema.

It would be desirable to further reduce the morbidity of the axillary sentinel lymph node biopsy if instrumentation were available to allow the sentinel lymph node to be identified and removed percutaneously with as little effect as possible to the surrounding tissue structure. The apparatus described in this patent can be introduced percutaneously through a small skin opening and directed to the sentinel lymph node thus eliminating open surgical exploration. Consequently, sentinel lymph node biopsy could be accomplished as an office procedure, eliminating hospitalization and minimizing the recovery period.

The elements of a percutaneous sentinel lymph node biopsy are as follows: The tumor site in the breast is injected with a radioisotope (such as technicium 99m labeled sulfur colloid) which travels via the lymphatic channels to the sentinel lymph node. The sentinel lymph node then becomes radioactively visible, or "hot." The apparatus hereafter described is able to identify or locate the radioactive lymph node through auditory and other signals, indicating when the apparatus is adjacent to the sentinel lymph node. The apparatus is further able to then characterize or "visualize" the surrounding tissue with the associated ultrasound portion of the apparatus. It is important to identify the associated structures adjacent to the lymph node, because relatively large blood vessels (arteries, veins,) and nerves traverse the axilla. With the combination of percutaneous Geiger counter identification and percutaneous ultrasound identification, the sentinel lymph node can be identified and biopsied without entering a major blood vessel or severing a major nerve.

With a small entry site, no suturing would be required (the procedure would be percutaneous), and the patient could be sent home with a simple band-aid over the axillary entry site. The following day, the patient would receive the results of the percutaneous sentinel lymph node biopsy determining whether or not metastatic disease is present or absent in the sentinel lymph node draining the affected breast.

Instruments are known in the prior art which could be adapted to perform some of the procedures outlined above. For example, U.S. Pat. No. 5,111,828 to Kornberg et al. discloses a percutaneous excisional breast biopsy device having a cannula, open distal and proximal ends, and a sharp cutting surface on the distal end. A stylet extends through the cannula and includes a distal puncturing end. A localization guide wire is used to direct the instrument to a biopsy site. The cannula is moved distally to cut a desired tissue specimen, after which a descending element is pushed to the distal end of the tissue specimen, then pulled proximally to sever the specimen completely from surrounding tissue.

A significant disadvantage of the Kornberg approach is that only one tissue sample may be obtained for each insertion of the instrument into the patient's body to the biopsy site. Once the descending element has been pulled to sever the tissue sample, there is no opportunity to repeat the procedure while the instrument remains in place. Also, no means is provided to ensure that tissue to be sampled is drawn toward the distal end of the cannula 2 (or "actively captured"), thereby reducing tissue sampling efficiency.

The present invention lacks the disadvantages and shortcomings of the prior art and provides an improved method and device for percutaneous excisional tissue biopsy. The present invention may be used for purposes others than percutaneous biopsy. For example, the device may be used for general organ and tissue removal through a trocar to perform various laparascopic procedures including splenectomy, nephrectomy, appendectomy and liver removal. The device may also be used laparascopically through a trocar to remove abnormal growths such as polyps.

SUMMARY OF THE INVENTION

This invention provides an inventive tissue sampling probe which offers many advantages over probes available in the prior art. Unexpectedly superior results are obtained in connection with the retrieval of intact tissue specimens, because of a unique combination of cutting features, including, for example, the employment of an electrosurgical cutting element and a vacuum assist in one preferred embodiment. A particularly important feature of the invention is the ability to manipulate the electrosurgical cutting element to cleanly sever the distal end of the tissue specimen. In certain embodiments, this is accomplished without any cutting impact on surrounding tissue. The versatility of the invention permits its use in many applications, including, for example, breast biopsies, intraoperative staging, laparoscopic surgery, and lymphadenectomy procedures.

More particularly, the invention provides a tissue sampling apparatus which comprises a tubular body having a primary lumen for receiving a tissue sample. The tubular body includes a distal end and a proximal end. An electrosurgical cutting element is provided, which is non-rotating during the cutting procedure in order to preserve the integrity of the tissue samples, though it may be rotatably pivoted across the tubular cross-section at the conclusion of the cutting process in order to sever the distal end of the tissue sample. In certain preferred embodiments, the electrosurgical cutting element comprises a wire disposed distally of the distal end of the tubular body. A means for drawing tissue to be sampled into the primary lumen is also provided, whereby the electrosurgical cutting element cuts the tissue to capture an intact tissue sample core within the primary lumen.

In a preferred embodiment, the means for drawing tissue into the lumen comprises a source of vacuum pressure for drawing a vacuum through the primary lumen, the vacuum pressure in the primary lumen drawing tissue to be sampled into the primary lumen and the electrosurgical cutting element cutting the tissue to capture an intact tissue sample within the primary lumen. The vacuum pressure then acts to transport the specimen proximally through the primary lumen to a tissue receptacle.

In one particular aspect of the invention, the tubular body is relatively flexible, rather than relatively rigid, so that the tubular body is steerable to obtain tissue samples from any desired location on the wall of a tissue cavity. In such an embodiment, the apparatus is deliverable to the tissue cavity, which is typically a void formed by the removal of tissue during a biopsy procedure, using a percutaneous access device.

In another particular aspect of the invention, a method of capturing a body tissue sample using a tissue sampling apparatus is provided, wherein the tissue sampling apparatus comprises a tubular body having a lumen extending therethrough, a distal end, an electrosurgical cutting element disposed distally of the distal end of the tubular body, an actuator for moving the cutting element, and an electrocautery generator. The method comprises the steps of activating the electrocautery generator to energize the electrosurgical cutting element, advancing the tubular body through a tissue portion a desired distance so that the energized electrosurgical cutting element cuts a tissue sample core as the tissue sample enters the lumen, and actuating the electrically energized cutting element so that it moves across at least a portion of the cross-sectional area of the tissue sample core at its distal end. This movement of the cutting element functions to sever the distal end of the tissue sample to thereby capture the tissue sample core in a substantially intact condition within the tubular body lumen.

The invention, together with additional features and advantages thereof, may best be understood by reference to the following description taken in conjunction with the accompanying illustrative drawing.

BRIEF DESCRIPTION OF THE DRAWING

FIG. 15 is a perspective view similar to that of FIG. 1, illustrating a third preferred embodiment of the inventive tissue sampling device;

FIG. 16 is a perspective view of the distal or business end portion of the FIG. 15 embodiment;

FIG. 17 is a perspective view similar to that of FIG. 16, illustrating the conductive cutting hoop of the invention actuated to a drawn severing position;

FIG. 18 is a perspective view similar to that of FIG. 1, illustrating a fourth preferred embodiment of the inventive tissue sampling instrument;

FIG. 19 is a perspective view of the distal or business end of the embodiment illustrated in FIG. 18;

FIG. 28 is a perspective view similar to that of FIG. 23, illustrating the tissue sampling instrument in a pre-sampling condition;

FIG. 29 is a perspective view of a stand-alone sensing probe which may be used in connection with the embodiment of FIG. 28;

FIGS. 30, 30*a*, 30*b* are perspective views of a multi-vision probe which may be used in connection with the embodiment of FIG. 28;

FIG. 33 is a perspective view of a seventh preferred embodiment of the inventive tissue sampling instrument, which incorporates a mechanical tissue removal system; and FIG. 34 is a cross-sectional view of the tissue acquisition device illustrated in FIG. 33.

DESCRIPTION OF THE INVENTION

Figure 1:
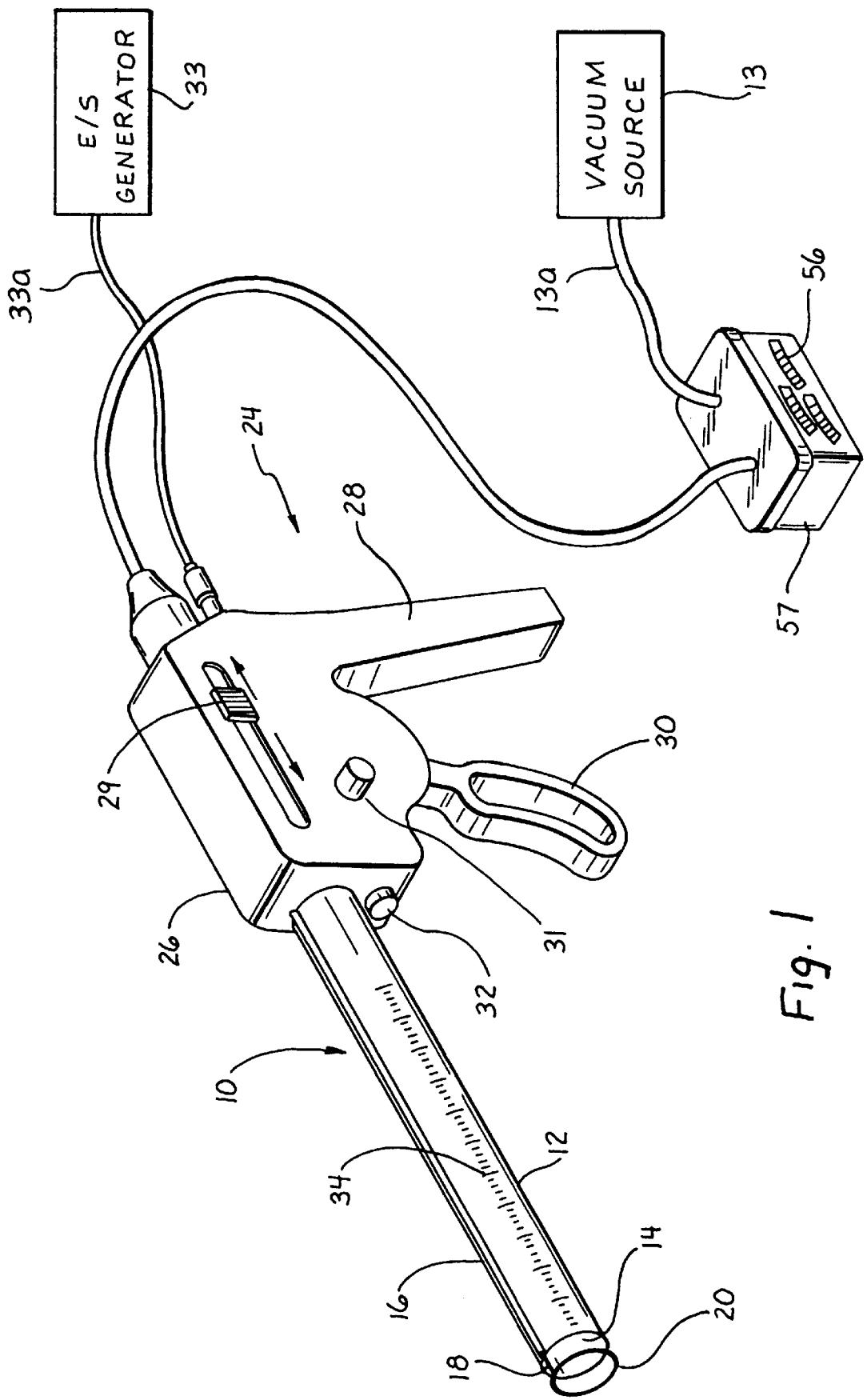
FIG. 1 is a perspective view of a first preferred embodiment of the inventive tissue sampling instrument.
Figure 2:
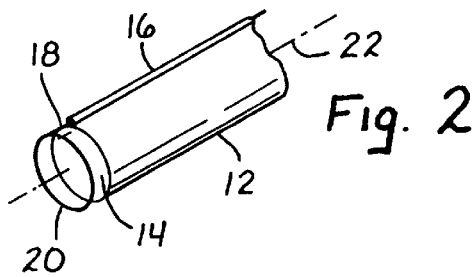
FIG. 2 is a perspective view illustrating the distal end of the inventive instrument shown in FIG. 1.

Referring now more particularly to FIGS. 1–8, a first preferred embodiment of the invention is shown. The inventive tissue sampling probe 10 comprises a tube 12 having a primary lumen 14 and a secondary lumen 16. Extending axially through the secondary lumen 16 is a support stem 18, preferably comprised of an electrically conductive metallic wire, which is joined at its distal end to a conductive cutting loop 20.

The tube 12 is connected, at its proximal end, to a source of vacuum 13, which is adapted for selectively drawing a vacuum through the primary lumen 14. The tube 12 is preferably fabricated of a non-conductive radiolucent or radiodense biocompatible material, such as plastic or epoxy, and preferably has a round cross-section, though other tube shapes may be used as well. The material may also be electrically conductive if its entire outside surface area is covered with an electrically insulative material (not shown).

Figure 3:
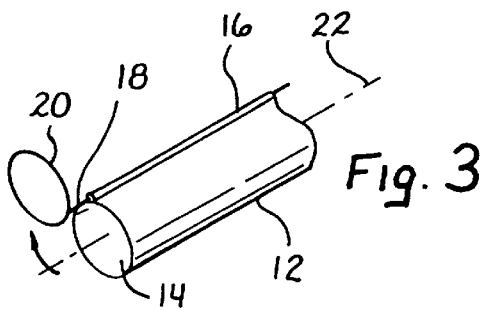
FIG. 3 is a perspective view similar to that of FIG. 2, illustrating the conductive cutting hoop of the FIG. 1 embodiment displaced in a first direction.
Figure 4:
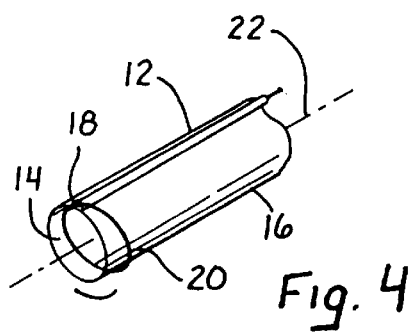
FIG. 4 is a perspective view similar to FIGS. 2 and 3, illustrating the conductive cutting hoop in the process of being displaced from the first cutting direction to a second cutting direction opposite to the first cutting direction shown in FIGS. 3 and 3*a*.

As shown in FIGS. 3 and 4, the conductive cutting loop 20 may be pivoted rotationally in a direction transverse to the longitudinal axis 22 of the tube 12, from a rightmost position (FIG. 3) to a leftmost position (FIG. 4). This pivoting action is created by rotation of the support stem 18 using an actuator 24 disposed at a proximal end of the inventive tissue sampling probe 10 (FIG. 1). The actuator 24 preferably comprises a housing 26, a fixed handle 28, a loop advancement slide knob 29, a trigger 30, a vacuum override switch 31, and an electrosurgical energy/vacuum actuation switch 32. The housing 26 encloses a spring mechanism (not shown) for joining the trigger 30 and the support stem 18 so that when the trigger 30 is squeezed in a conventional manner, against the bias of the spring mechanism, the support stem 18 is rotated to pivot the conductive cutting loop 20 to the position shown in FIG. 3. When the trigger 30 is opened in the direction opposite of the squeezing direction, against the bias of the spring mechanism, the support stem 18 is rotated to pivot the conductive loop 20 to the position shown in FIG. 4. Any other type of desired conventional actuator may be used as well, including manual, motor-driven, and electronically-driven mechanisms.

An important aspect of the invention is the use of an electrocautery generator 33 (FIG. 1). The electrical energy from the electrocautery generator is conducted along electrical line 33a to the support stem 18 and from there to the conductive cutting loop 20 of the apparatus shown in FIG. 1. Additionally, the source of vacuum 13 is also employed to selectively draw a vacuum through a vacuum line 13a and along the tissue receiving lumen 14 formed by the tube 12.

Therefore, in operation, with respect to the embodiment of FIG. 1, the electrocautery generator is activated using the actuation switch 32 to electrically activate the conductive cutting loop 20. When the actuation switch 32 is depressed, the vacuum source is simultaneously activated to draw a vacuum through the lumen 14. Once these systems are operational, the tube 12 is advanced through tissue to obtain the desired tissue sample. In the preferred embodiment, depth marks 34 are disposed axially along the exterior surface of the tube 12 in order to assist the physician in determining when the tube 12 has been advanced to the desired position.

In its preferred operational mode, the energized conductive cutting loop 20 functions to cut a tissue sample having approximately the same diameter or cross-sectional shape as that of the tube 12. Surprisingly, the inventors have found that the combination of an activated electrocautery cutting element and the drawing of a vacuum at the cutting site proximally through the tissue receiving lumen 14 improves and expedites the tissue capture process, to an unexpected degree. While soft tissues typically tend to move away from a severing instrument, such as a knife blade, the vacuum tends to counteract this movement, resulting in a startlingly improved cutting process.

Once a sample of adequate length has been secured, the conductive cutting loop 20 is electrically actuated for cutting and mechanically actuated to rotatably pivot both rightwardly and leftwardly, as shown in FIGS. 3 and 4, using the trigger actuator 24. This pivoting action functions to sever the distal end of the tissue sample (not shown) from the remaining body tissue, thereby completing the capture process. Furthermore, as illustrated in FIG. 1, a tissue reservoir or vacuum trap 57 may be employed in the vacuum line proximally of the sampling probe 10 for receiving and storing tissue samples drawn proximally through the sampling device body by the vacuum source 13.

An important aspect of the invention, critical to the functionality of the instrument shown in FIG. 1, is that the annular space within the lumen 16 surrounding the support stem 18 serves as a vent port when the tissue sample is drawn out of the body by the negative pressure created by the vacuum source 13, thereby repressurizing the space in the tube lumen 14 distal of the tissue sample. Without this repressurization capability, trouble-free operation in obtaining the desired tissue samples is unlikely because of pressure gradient variations. It should be noted, also, that actuation of the vacuum override switch 31 permits operation of the device without the application of vacuum pressure, if desired.

Figure 5:
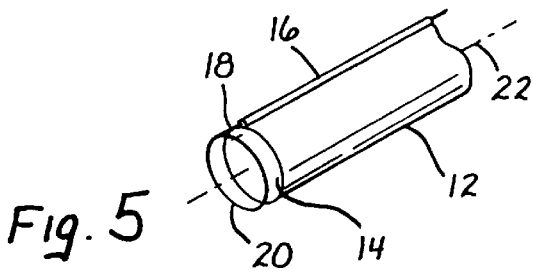
FIG. 5 is a perspective view of a modified embodiment of the distal end of the inventive instrument, illustrating the conductive cutting hoop in a retracted position.
Figure 6:
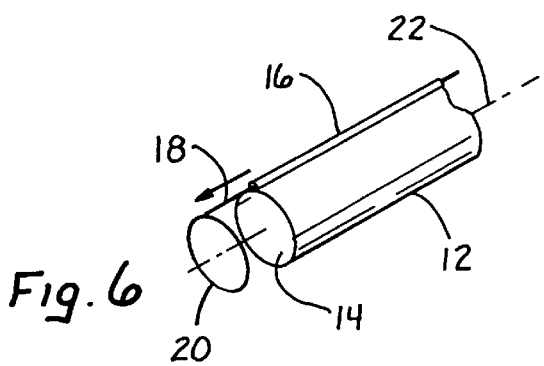
FIG. 6 is a perspective view of the modified embodiment of FIG. 5, illustrating the conductive cutting hoop in an axially extended position.

As illustrated in FIGS. 5–6, the support stem 18 may be actuated axially as well as rotationally, between a proximal position, as shown in FIG. 5, wherein the conductive cutting loop 20 is retracted, and a distal position, as shown in FIG. 6, wherein the conductive cutting loop is extended. The loop advancement slide knob 29, which is fixedly attached to the support stem 18 by means of a conventional connective element enclosed within the housing 26, is utilized to axially advance and retract the cutting loop. Advancing the cutting loop 20 axially provides an alternate means of cutting tissue in an axial direction without requiring the entire sampling probe 10 to move axially as well.

Figure 7:
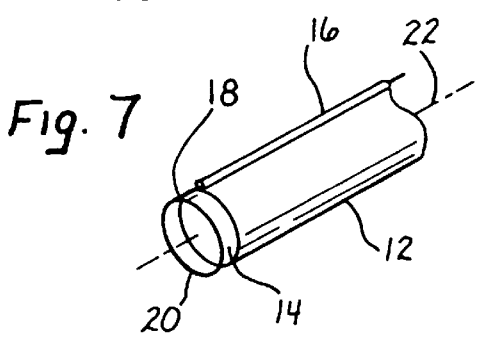
FIG. 7 is a perspective view of a second modified embodiment of the distal end of the inventive instrument, wherein the support stem for the conductive cutting hoop, shown in its retracted position, is preformed to a predetermined non-linear shape.
Figure 3A:
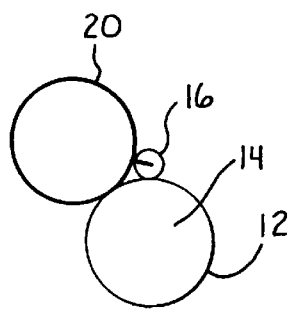
FIG. 3*a* is an end elevation view illustrating the conductive cutting hoop displaced in the first cutting direction.
Figure 8:
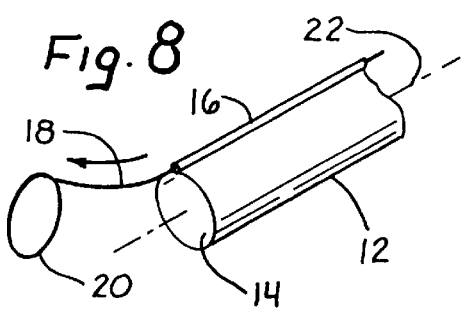
FIG. 8 is a perspective view of the second modified embodiment, similar to FIG. 7, showing the conductive cutting hoop in an extended non-linear position.
Figure 4A:
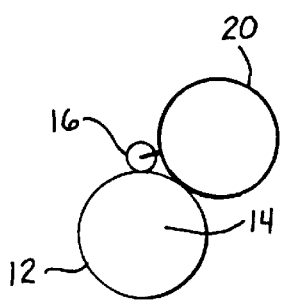
FIG. 4*a* is an end elevation view similar to that of FIG. 3*a*, illustrating the conductive cutting hoop displaced in the second cutting direction.

An advantageous optional feature of the present invention is illustrated in FIGS. 7 and 8, wherein the support stem 18 has been preformed to permit movement of the cutting loop 20 in a non-straight direction as it is advanced into the tissue, as shown in FIG. 8. Such a feature may be important if the tissue to be sampled is disposed to the side of the entry path for the device 10, such as, for example, when a lesion to be sampled is disposed in a side wall of a body cavity or conduit.

Figure 9:
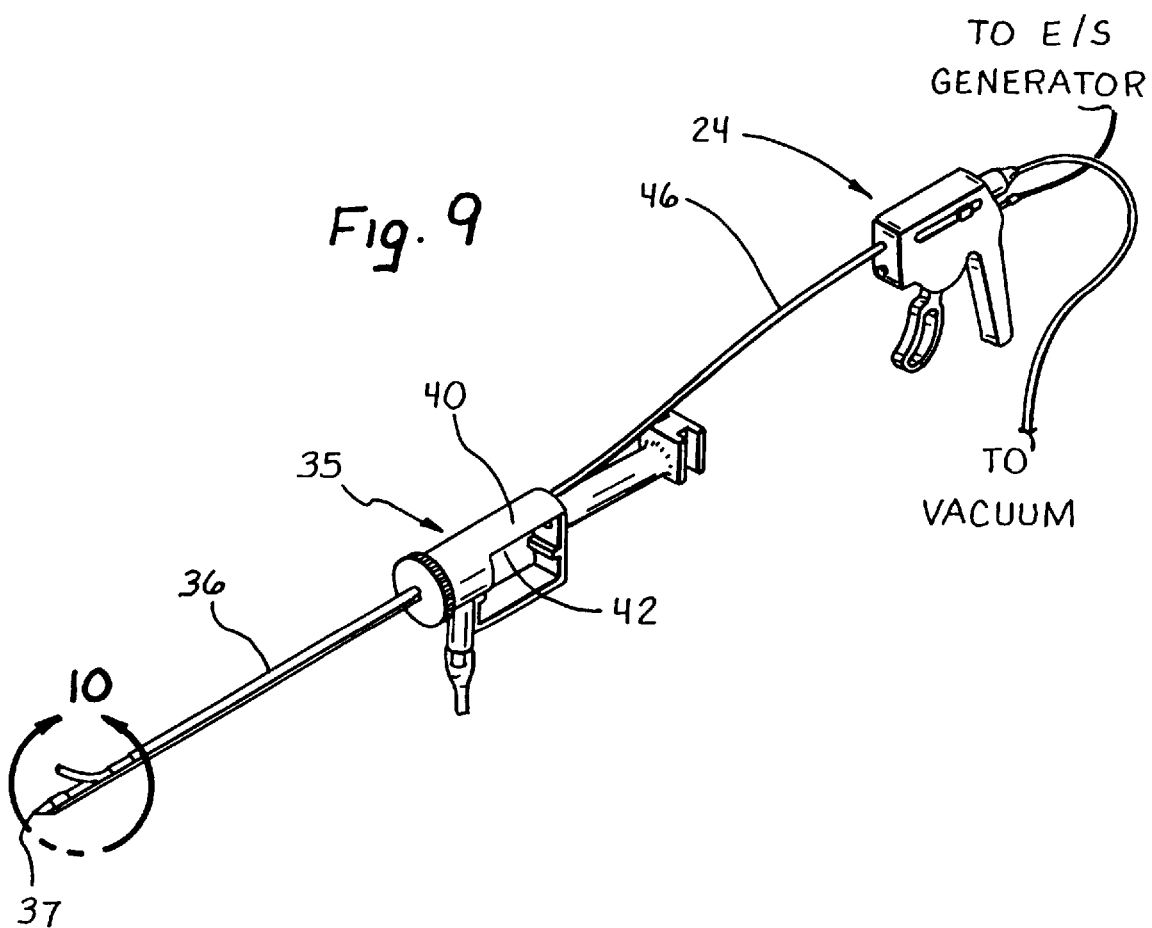
FIG. 9 is a perspective view of a second preferred embodiment of the inventive tissue sampling instrument, illustrating a flexible probe which is adapted for percutaneous deployment into a body cavity trough an established working port.
Figures 10, 10A:
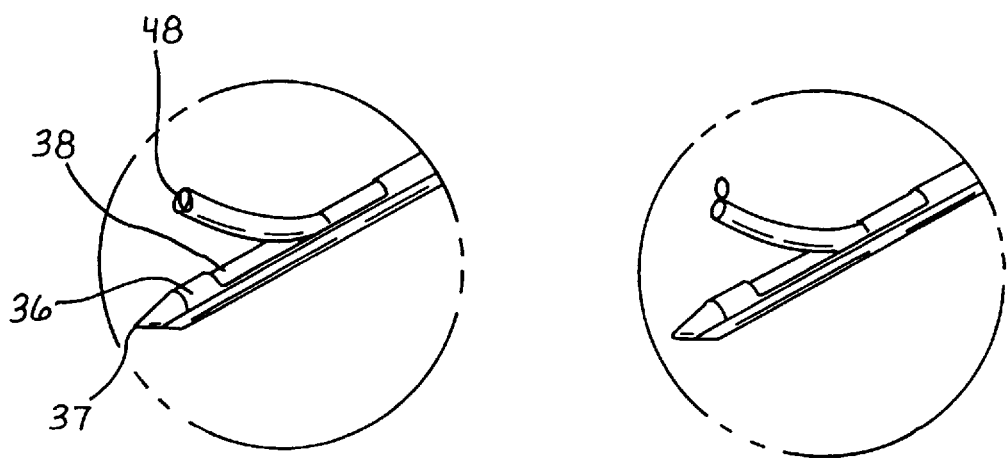
FIGS. 10 and 10*a* are perspective views illustrating the distal end of the embodiment shown in FIG. 9.

FIGS. 9–10 illustrate a particular embodiment of the invention which may utilize a modified version of the instrument shown in FIGS. 1–8, or which may alternatively utilize other similar devices such as the embodiments shown in FIGS. 13–28 and described infra. As discussed supra with respect to the embodiment shown in FIGS. 7–8, it is often the case that it is desirable to sample selected areas of a cavity wall from within the cavity, and for such a purpose a probe capable of non-axial movement, and preferably having flexible characteristics, is necessary. In one preferred implementation, an automatic core biopsy device 35 of the type disclosed in U.S. patent application Ser. No. 08/217, 246, filed on Mar. 24, 1994, and application Ser. No.

08/386,941, filed on Feb. 10, 1995, both of which are assigned to the assignee of the present application, and are herein expressly incorporated by reference, is employed. Such a device is presently commercially available from Biopsys Medical, Inc., of Irvine, Calif., the assignee of the present application, under the trademark MAMMOTOME. The automatic biopsy device 35 comprises a hollow outer piercing needle 36 having a pointed tip 37 and a tissue receiving notch 38. A proximal tissue cassette housing 40 includes a cassette receiving aperture 42 and a vacuum port 44. As discussed in the prior patent applications Ser. Nos. 08/217,246 and 08/386,941, the biopsy device 35 is adapted to enter the patient's body using commercially available imaging guidance systems commonly used in the medical field for accurate positioning of a variety of medical devices with respect to a patient and with respect to a lesion within a patient. For example, a stereotactic motorized biopsy needle positioning system, such as that disclosed in U.S. Pat. No. 5,240,011, issued on Aug. 31, 1993, to Michael Assa, which is expressly incorporated herein by reference, may be used. The suspect lesion within the tissue to be sampled is targeted according to the instructions provided with the stereotactic guidance system. The stereotactic guidance system enables an operator to advance the pointed tip 37 until it is adjacent to the specific tissue region to be sampled.

Alternatively, other guidance systems may be used in conjunction with the inventive device, such as ultrasound, radiolabelling with detector, or localization wire.

Figure 11:
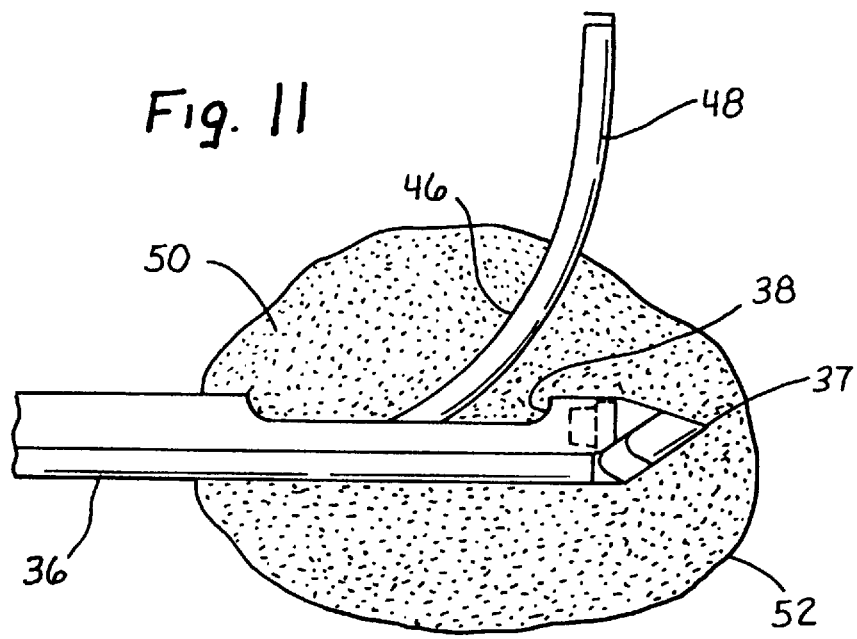
FIG. 11 is an enlarged elevational schematic view of the distal portion of the flexible probe illustrated in FIG. 9.
Figure 12:
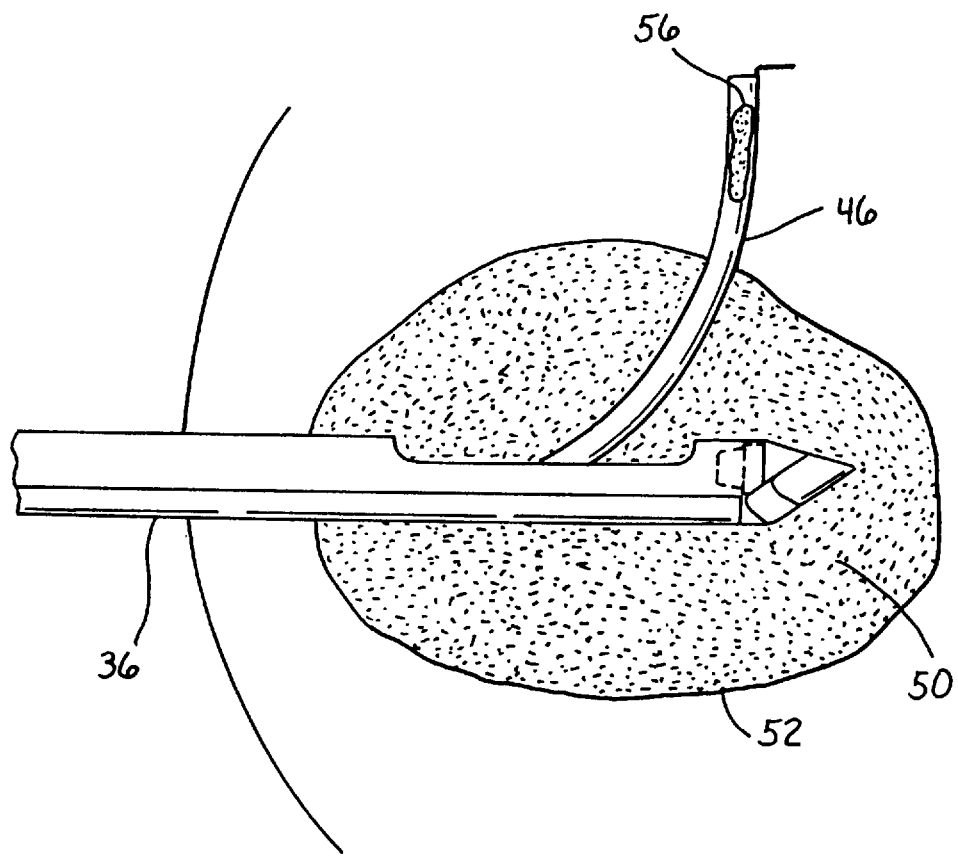
FIG. 12 is an elevational view similar to that of FIG. 11, illustrating the receipt of a tissue specimen within the distal end of the flexible probe.

A flexible sampling device 46 having a distal end 48 may be percutaneously delivered to the site of a lesion to be sampled by inserting it through the automatic core biopsy device 35. Preferably, the sampling device 46 is received by the cassette receiving aperture 42 and extends through the lumen of the hollow outer piercing needle 36, exiting into a body cavity 50 (FIGS. 11 and 12) through the tissue receiving notch 38. Because of its flexibility and torqueability, the sampling device 46 is capable of sampling any selected area of the cavity wall. To do so, as illustrated in FIG. 11, the end of the sampling device 46 extends into the cavity wall 52 to a depth predetermined by the operator to be appropriate. The distal end of the sampling device 46, or "business end", may be constructed in accordance with the principles illustrated in FIG. 1, or, alternatively, any of the other embodiments illustrated in FIGS. 13–28, and is preferably configured to ensure that the effective diameter of the incision is less than about 7 mm, in order to hopefully avoid the need for stitches. Larger diameter sampling devices are certainly feasible, however. Thus, the tube 12 of the device illustrated in FIG. 1 may be constructed of a substantially rigid electrically conductive biocompatible material, to create a substantially rigid probe device, or alternatively, it may be constructed of a flexible biocompatible material like that shown in FIGS. 10 and 11 (flexible sampling device 46).

Figure 13:
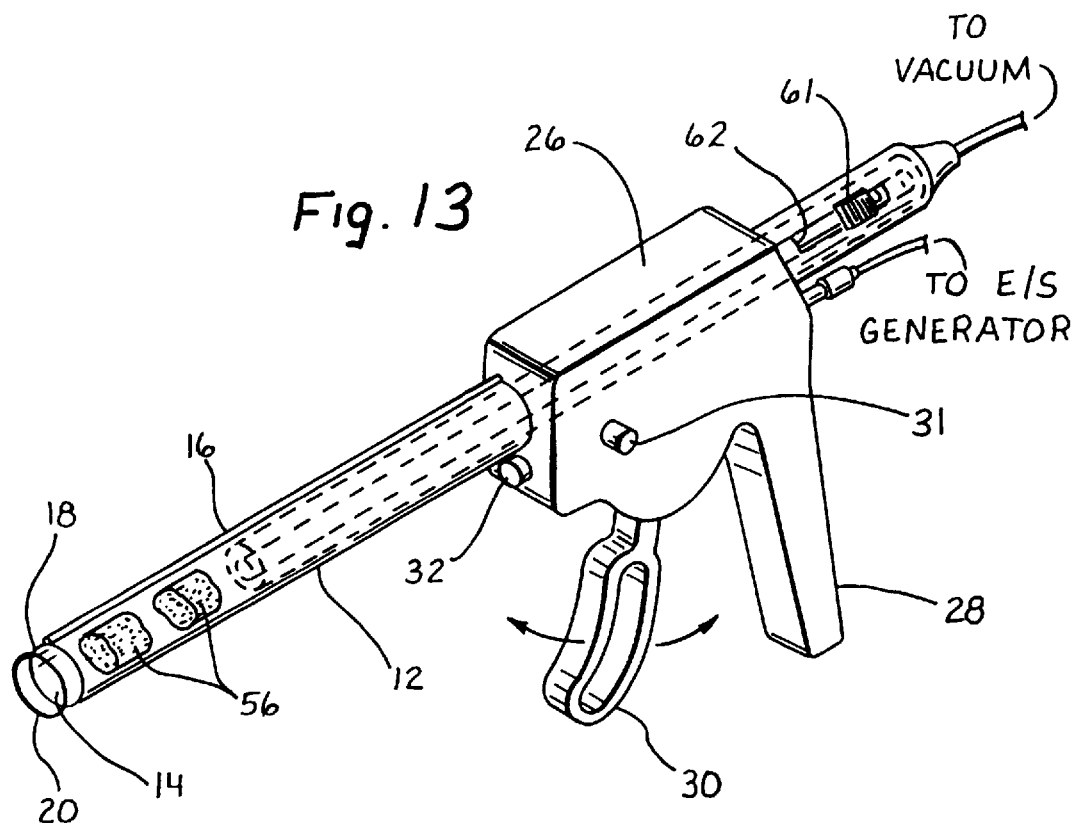
FIG. 13 is a perspective view of the embodiment of FIG. 1, illustrating an optional inventive feature for accommodating a plurality of tissue samples.
Figure 14:
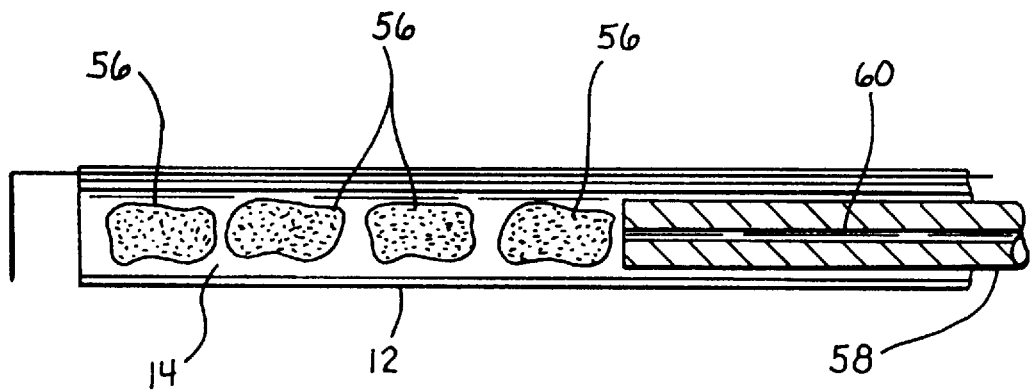
FIG. 14 is schematic cross-sectional view illustrating the interior of a tubular portion of the tissue sampling device shown in FIG. 13, illustrating the use of a movable stop plunger to permit the receipt of multiple tissue specimens and to prevent the specimens from being suctioned proximally to a source of vacuum utilized to draw tissue samples into the inventive device.

As illustrated in FIGS. 13 and 14, the lumen 14 may be configured to accept a plurality of sequentially obtained tissue samples during a single medical procedure, with only a single entry and exit of the device into and out of the patient's body. Optionally, a movable stop plunger 58 having a vacuum lumen 60 extending therethrough may be employed, wherein the stop plunger is arranged to be progressively moved proximally as specimens are obtained, to permit space for the additional specimens while at the same time prohibiting the specimens from being drawn through the tube 12 to the vacuum source. Additionally, it may be desirable to coat the inner surface of the tube 12 with a hydrophyllic or slick coating in order to facilitate transport of the tissue sample. A stop plunger lever 61 (FIG. 13), disposed on a proximal portion of the housing 26, is axially slidable within a slide channel 62 to axially move the stop plunger 58.

Many other embodiments may be employed other than the embodiment illustrated in FIGS. 1 and 13. For example, a modified embodiment is illustrated in FIGS. 15–17, wherein all elements corresponding to those of the embodiment of FIG. 1 are designated by like reference numerals, succeeded by the letter "a". In this embodiment, the conductive cutting loop 20*a* is comprised of a pair of wires 120 and 220, both of which extend proximally through the secondary lumen 16*a* in the form of support stems 118 and 218, respectively. As in the prior embodiment, the wires 120 and 220 are capable of conducting electrical energy for electrocautery purposes. FIG. 16 illustrates the wires 120 and 220 in their rest position, while FIG. 17 illustrates the wires after the support stems 118 and 218 have been pulled proximally by pulling a slide lever 63 in a proximal direction, which slide lever 63 is operatively connected to the support stems 118 and 218. Pulling the support stems 118 and 218 proximally causes the wires to close the end of the tube 12*a* and thereby sever the distal end of the tissue sample contained with the tube lumen 14*a*, in a manner similar to that of the loop 20 in the FIG. 1 embodiment. An important difference between the FIG. 1 and FIGS. 15–17 embodiments is that the drawing of the two wires 120 and 220 to a closed position functions to sever only the distal end of the tissue sample without cutting and thereby injuring surrounding tissue, unlike the conductive cutting loop 20 of FIG. 1, which, as shown in FIGS. 3 and 4, substantially impacts surrounding tissue during the rotational severing process.

Still another embodiment of the inventive apparatus is illustrated in FIGS. 18 and 19, wherein like elements to those of previous embodiments are designated by like reference numerals, succeeded by the letter "c". In this embodiment, a partial wire hoop 20*c* is utilized, which is shown in solid line in its rest position, and in phantom in its actuated position. To sever the distal end of the tissue sample, the partial hoop 20*c* is rotated from the rest position to the actuated position, by rotating the support stem 18*c* using an actuator 24*c*, which may be identical to actuator 24 illustrated in FIG. 13, if desired, following which the body tube 12*c* is rotated by 180 degrees to complete the tissue severing task. In this embodiment, unlike the embodiment of FIG. 1, for example, the hoop 20*c* does not function as the axial cutting element as the instrument is advanced into the target tissue. Rather, the tube 12*c* is electrically conductive in this embodiment, and, in order to ensure safe handling of the instrument, is therefore covered by an insulative sleeve 64 along its entire length (FIG. 19), except at its distal end. The uncovered distal end 65 of the tube 12*c* is therefore electrically charged and exposed, so that the distal end 65 functions as an electrosurgical axial cutting element as the instrument is advanced through the tissue.

Figure 20:
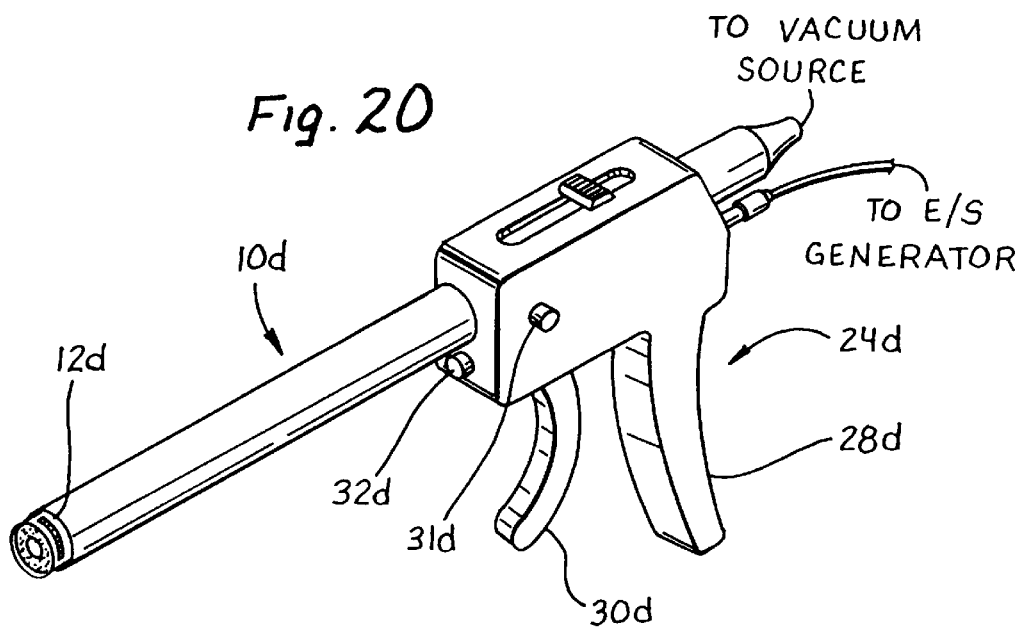
FIG. 20 is a perspective view similar to that of FIG. 1, illustrating a fifth preferred embodiment of the inventive tissue sampling device.
Figure 21:
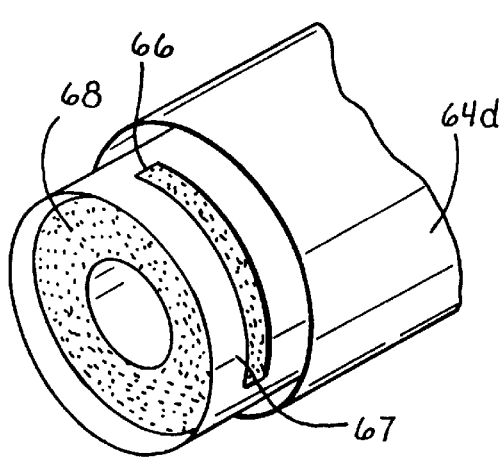
FIG. 21 is a perspective view of the distal end portion of the embodiment illustrated in FIG. 20, wherein the distal end is preformed to a predetermined shape.
Figure 22:
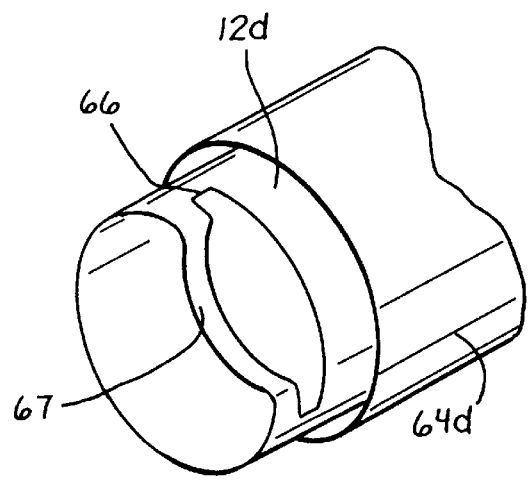
FIG. 22 is a perspective view similar to FIG. 21, illustrating the retraction of an inner cannula and subsequent relaxation of the distal end to its predetermined shape.

Yet another embodiment of the inventive apparatus is shown in FIGS. 20–22, wherein like elements to those of previous embodiments are designated by like reference numerals, succeeded by the letter "d". In FIG. 20, the conductive tubing body 12*d* is illustrated, wherein a circumferential slit 66 has been partially cut through the tube 12*d* near its distal end. A band of tubing material 67 disposed distally of the slit 66 is then bent inwardly and stress relieved in the position shown in FIG. 22. Following this, as illustrated in FIG. 21, an inner coaxial tube 68 is inserted into the tubing body 12*d* to force the material band 67 open. At this point, the instrument 10*d* is ready to use. When the tube 12*d* has been advanced into a patient's body to obtain a tissue sample, the inner tube 68 is removed to cause the band of material 67 to snap inwardly to its natural stress relieved position, as shown in FIG. 22. Since the tubing 12d, and therefore the material band 67 are electrically energized, the motion of the band of material 67 inwardly functions to partially cut off the distal end of the tissue sample. The tube 12d is then rotated 180 degrees to completely sever the tissue sample.

Figure 27:
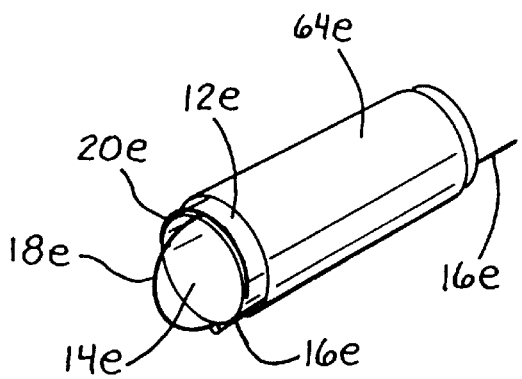
Figure 32:
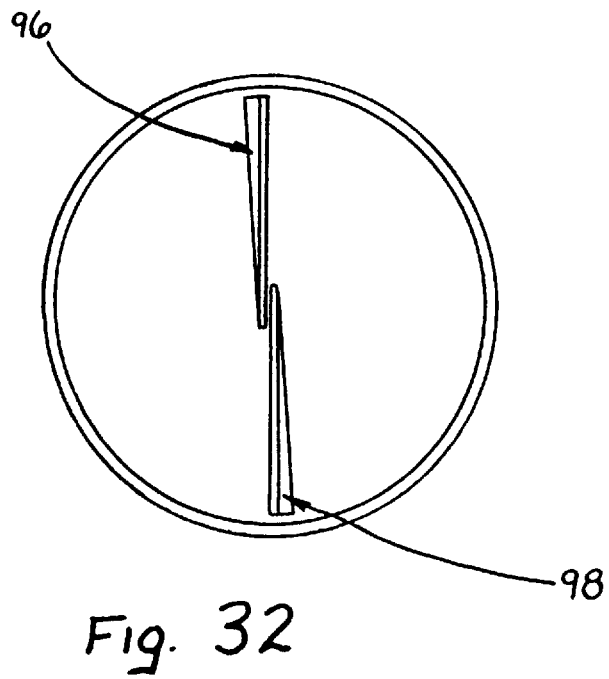
FIG. 32 is an end view of the endoscopic shears illustrated in FIG. 31.

FIGS. 23–27 illustrate still another embodiment of the inventive device, wherein like elements to those of previous devices are designated with like reference numerals, succeeded by the letter "e". In this embodiment, a wire loop 20e is adapted to pivot from one side of the tube 12e (FIG. 24) to the other side of the tube 12e (FIG. 27). As with the previous embodiments, rotation of the wire loop 20e, which is energized by the electrocautery generator (not shown), severs the distal end of the tissue sample being captured, which capture is assisted by the simultaneous application of a suction to the proximal end of the lumen 14e. Again, the design of the wire loop 20e of this embodiment advantageously minimizes damage to tissue surrounding the tissue to be captured.

Figure 23:
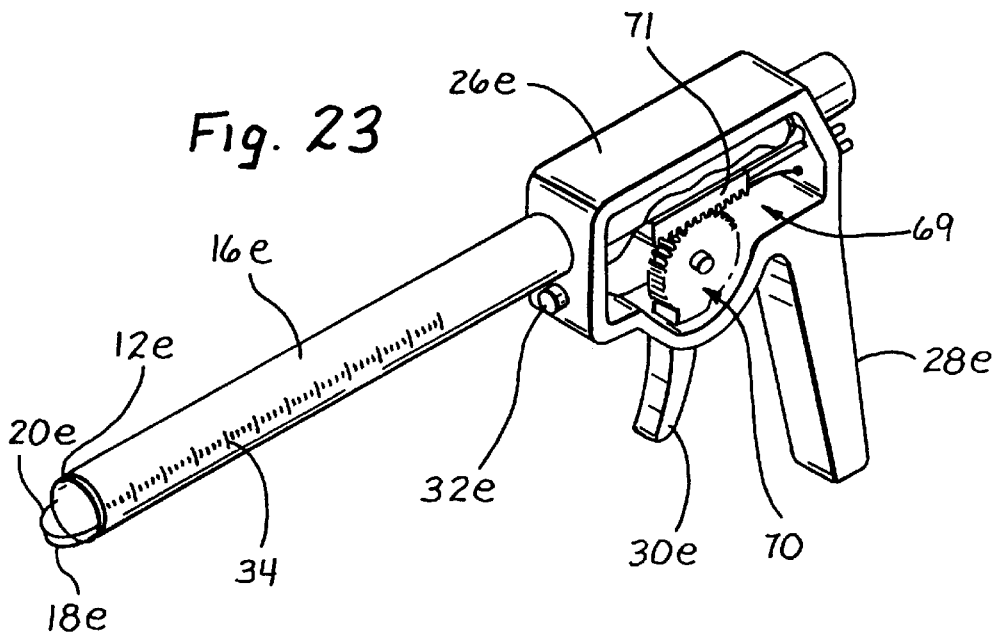
FIG. 23 is a perspective view similar to that of FIG. 1, illustrating a sixth preferred embodiment of the inventive tissue sampling device.
Figure 24:
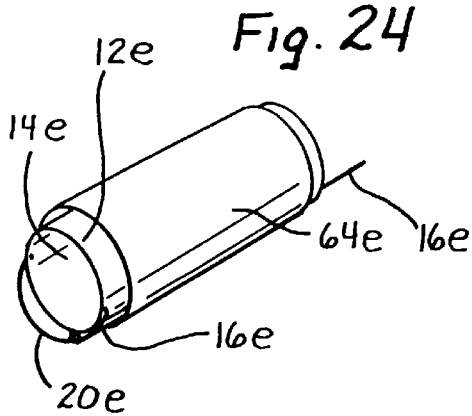
FIGS. 24–27 are perspective views of the distal end portion of the FIG. 23 embodiment, in various operating positions.
Figure 25:
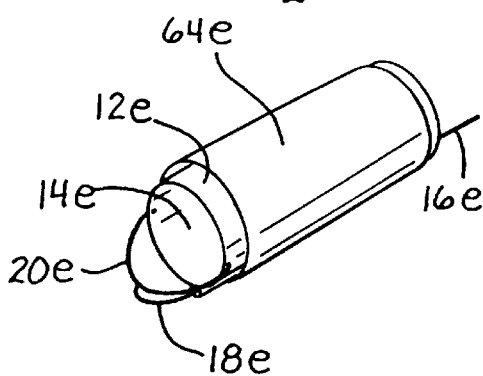
Figure 26:
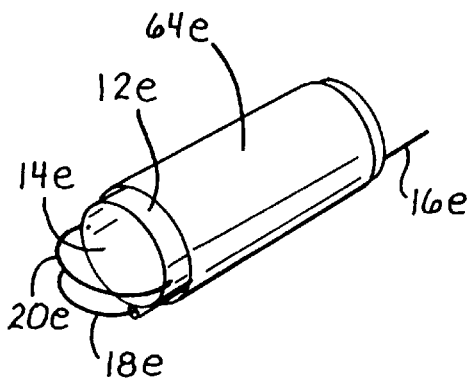

In the FIG. 23 embodiment, the housing 26e is shown cut away, so that the actuating mechanism 69 for the hoop 20e is visible. For this preferred actuating mechanism, an upper portion 70 of the bidirectional trigger 30e comprises a pinion, having teeth which engage a rack 71, which in turn is connected to the support stem 18e to drivingly rotate the hoop 20e in either of two directions. Optionally, this actuating mechanism 69 may be utilized in any of the illustrated embodiments, if desired. On the proximal end of the housing 26e, a pair of fittings are disposed for attachment to corresponding control lines 86 and 88, respectively (illustrated in FIG. 28).

A particularly advantageous aspect of the invention is its ability to be used in connection with sensing probes for identifying and locating desired tissue to be sampled. For example, ultrasound probes or radiation detecting (Geiger) probes may be employed, such as those disclosed in U.S. Pat. Nos. 4,959,547, 5,036,201, 5,119,818, 5,148,040, 5,170,055, and 5,246,005, which are assigned to Care Wise Medical Products Corporation of Morgan Hill, Calif., and are herein expressly incorporated by reference. Referring particularly to FIGS. 28–30, wherein like elements to those of previous devices are designated with like reference numerals, succeeded by the letter "g", a tissue sampling probe, or soft tissue acquisition device 10g is illustrated, having a tube 12g, a primary lumen 14g, a secondary lumen 16g, a support stem 18g, and a conductive cutting loop 20g. The cutting loop 20g may comprise any of the types of cutting loops disclosed in the previous embodiments, as desired. A handle 24g is preferably joined to a proximal end of the tube 12g, and includes a trigger 30g and a through hole 78, which is configured to receive a sensing probe 80 or 82 (FIGS. 29 and 30). The handle may be manually held, or may alternatively be held by a mechanical arm or fixed to a stereotactic platform or the like.

A stand alone sensing probe 80 is illustrated in FIG. 30, which may comprise either an ultrasonic probe or a geiger probe, both of which are conventionally known in the medical diagnostic arts. The probe 80 is specifically configured to mate into the through hole 78 of the soft tissue acquisition device 10g. Electronic control lines 84 extend from a proximal end of the probe 80 to appropriate control units, for receiving and processing information obtained by the probe.

Alternatively, a multi-vision probe, such as the probe 82 illustrated in FIG. 30, may be utilized. This type of probe is capable of functioning both as an ultrasonic probe and as a geiger probe, and has two sets of control lines 86 and 88 for communicating with ultrasonic and geiger electronic control units, respectively.

Figure 31:
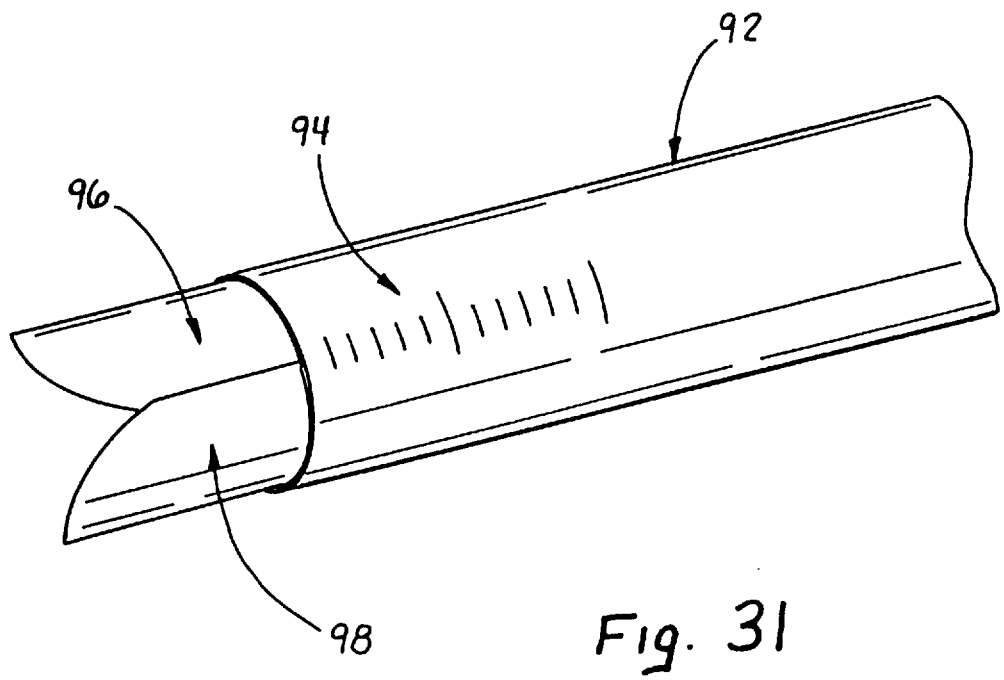
FIG. 31 is a side view of endoscopic shears which may be utilized in connection with the embodiment of FIG. 28.

In operation, a lesion (tissue) 90 to be sampled (FIG. 28) is located using a multi-vision probe 82 or a combination of stand-alone probes 80, which are disposed in the soft tissue acquisition device 10g. The geiger portion of the probe provides an X-Y location on the surface of the tissue to be sampled, while the ultrasonic portion provides depth information as well as X-Y location information. Then, the soft tissue acquisition device 10g is held in position, while the sensing probe(s) is (are) removed. Following location of the lesion 90, scissors 92 (FIG. 31) having depth marks 94 and blades 96, 98, may be used, if necessary, through the lumen 14g to dissect distally to a position within the tissue just proximal to the lesion 90 of interest. Then, the scissors 92 are removed from the lumen 14g, and the tissue acquisition device 10g is electrically energized and advanced to the predetermined depth. At this juncture, the end cutting loop 20g is utilized in a manner similar to that discussed in connection with previously disclosed embodiments to sever the distal end of the tissue specimen, following which suction is activated, using vacuum switch 31g, to transport the specimen proximally through the lumen 14g.

Referring now to FIG. 33 and 34, another embodiment of the inventive soft tissue acquisition device is provided, wherein like elements to those of previous devices are designated with like reference numerals, succeeded by the letter "i".

Although the use of negative pressure to withdraw the tissue specimens is preferred, the invention is broad enough to include other approaches for ensuring prompt and efficient retrieval of intact specimens. For example, as illustrated in FIGS. 33 and 34, a mechanical grasper 112 having a shaft 114 extending through a rear port 116 configured for working instruments, and the lumen 14i, is employed to grasp tissue using distal jaws 118, which are openable and closable by means of handles 120. In this embodiment, the trigger 30i may be pulled to simultaneously actuate the vacuum and electrosurgical generator, thereby causing the tissue sample to be severed, as described with respect to the aforementioned embodiments. Then, simultaneously with the severing process, the graspers 112 may be used to "grab" the tissue sample with the jaws 118, and to pull the sample proximally through the lumen 14i. Optionally, a "vacuum only" button 122 and an "electrosurgical power only" button 124 are disposed on the housing 26i so that the physician may elect to cut out either vacuum or electrosurgical power when pulling the trigger. The vacuum line is attached to a vacuum fitting 126 and the electrosurgical power line is attached to an electrosurgical fitting 128, both of which are disposed on the housing 26i. A particular advantage of this embodiment, in certain applications, is that there is no electrosurgical cutting hoop disposed distally of the cutting end of the tube 12i, so the instrument is ideally suited for retrieving samples from tissues which have been dissected away from the "parent" tissue, yet are still in the body. Such is often the case in laparascopic surgery applications.

While this invention has been described with respect to various specific examples and embodiments, it is to be understood that the invention is not limited thereto and that it can be variously practiced within the scope of the following claims.

What is claimed is:

1. A tissue sampling apparatus, comprising:

a tubular body having a primary lumen for receiving a tissue sample, the tubular body having a distal end, a proximal end, and a longitudinal axis; and an electrosurgical cutting element disposed at the distal end of the tubular body, said cutting element being movable, relative to said tubular body, in a direction transverse to said axis, across a cross-sectional area defined by the distal end of said tubular body, in order to sever a distal end of an intact tissue sample core captured within said primary lumen.

2. The tissue sampling apparatus as recited in claim 1, wherein the electrosurgical cutting element comprises a wire disposed distally of the distal end of the tubular body.

3. The tissue sampling apparatus as recited in claim 2, wherein said wire comprises a single substantially circular wire which is pivotable from side-to-side to sever a distal end of the tissue sample, thereby completely severing the tissue sample from surrounding tissue.

4. The tissue sampling apparatus as recited in claim 2, wherein the wire comprises a pair of wires which together are actuatable from a rest position to a severing position, the pair of wires together forming a substantially circular cutting element disposed circumferentially along a distal edge of the tubular body in said rest position, and the pair of wires being drawn together across the cross-sectional area in order to sever a distal end of the tissue sample, thereby completely severing the tissue sample from surrounding tissue.

5. The tissue sampling apparatus as recited in claim 2, wherein the wire comprises a single wire which is actuatable from a rest position to a severing position, the wire forming a substantially circular cutting element disposed circumferentially about a distal edge of the tubular body in the rest position, and the wire being drawn across the cross-sectional area of the distal end of the tubular body while being electrically energized in the severing position, the drawing motion of the wire across the cross-sectional area functioning to sever a distal end of the tissue sample, thereby completely severing the tissue sample from surrounding tissue.

6. The tissue sampling apparatus as recited in claim 2, wherein the wire comprises a single wire which is actuatable from a rest position to a severing position, the wire forming a semicircular cutting element disposed circumferentially along a portion of a distal edge of the tubular body in the rest position, and the wire being drawn across the cross-sectional area of the distal end of the tubular body while being electrically energized in the severing position, the drawing motion of the wire across the cross-sectional area functioning to sever a portion of the distal end of the tissue sample.

7. The tissue sampling apparatus as recited in claim 2, wherein the distal end of the tubular body comprises a second electrosurgical cutting element, the tubular body being constructed of an electrically conductive material and being further surrounded by an insulative jacket along its entire length except at its distal cutting end, the second electrosurgical cutting element being adapted to cut tissue, creating a tissue sample core, as the apparatus is advanced into a patient's body, and the electrosurgical cutting wire being adapted to sever a distal end of said tissue sample core.

8. The tissue sampling apparatus as recited in claim 2, and further comprising a support stem attached to said wire and disposed proximally thereof for supporting and controlling said wire, and a secondary lumen for receiving said support stem.

9. The tissue sampling apparatus as recited in claim 8, wherein the support stem is movable proximally to retract the wire cutting element in a proximal direction, and is movable distally to extend the wire cutting element in a distal direction.

10. The tissue sampling apparatus as recited in claim 9, wherein the support stem is preformed to allow movement of the wire cutting element in a non-linear direction as it is extended distally.

11. The tissue sampling apparatus as recited in claim 8, and further comprising a mechanical actuator for moving said support stem to thereby actuate said wire.

12. The tissue sampling apparatus as recited in claim 1, wherein the electrosurgical cutting element is also movable axially relative to said tubular body.

13. The tissue sampling apparatus as recited in claim 1, wherein the tissue sample core has a diameter substantially equal to an inside diameter of said tubular body.

14. The tissue sampling apparatus as recited in claim 1, and further comprising means for drawing tissue to be sampled into the primary lumen.

15. The tissue sampling apparatus as recited in claim 14, wherein said means for drawing tissue comprises a mechanical grasper having openable jaws which are adapted to extend through the primary lumen of said tubular body.

16. The tissue sampling apparatus as recited in claim 14, wherein said means for drawing tissue comprises a source of vacuum pressure for drawing a vacuum through the primary lumen.

17. The tissue sampling apparatus as recited in claim 16, and further comprising:

a support stem attached to said wire and disposed proximally thereof for supporting and controlling said wire;

a secondary lumen for receiving said support stem; and an annular space surrounding said support stem within said secondary lumen, said annular space functioning as a vent port, drawing air at ambient pressure distally therethrough to repressurize regions in said primary lumen distal to the tissue sample being drawn proximally through said primary lumen, said repressurization functioning to assist transport of said sample proximally through the primary lumen.

18. The tissue sampling apparatus as recited in claim 16, wherein said body lumen is adapted to accommodate a plurality of tissue samples, said apparatus further comprising a movable stop plunger disposed at the proximal end of the tubular body lumen, said movable stop plunger preventing the tissue samples from being drawn proximally to the vacuum pressure source, and being movable in a proximal direction as additional tissue samples are captured in order to expand the lumen space available to accommodate the tissue samples.

19. The tissue sampling apparatus as recited in claim 16, wherein said apparatus further comprises a housing portion, the housing portion comprising a first switch for simultaneously activating the source of vacuum pressure and an electrocautery generator for providing electrical current to said electrosurgical cutting element, a second switch for activating only the source of vacuum pressure, and a third switch for activating only the electrocautery generator.

20. The tissue sampling apparatus as recited in claim 16, and further comprising a tissue reservoir disposed proximally of said tubular body.

21. The tissue sampling apparatus as recited in claim 20, wherein said tissue reservoir is disposed in a vacuum pressure line between the tubular body and the source of vacuum pressure.

22. The tissue sampling apparatus as recited in claim 16, and further comprising a vacuum override switch for selectively cutting off the source of vacuum pressure.

23. The tissue sampling apparatus as recited in claim 1, wherein the tubular body is comprised of a non-electrically conductive material.

24. The tissue sampling apparatus as recited in claim 1, wherein said tubular body lumen is adapted to accommodate a plurality of tissue samples.

25. The tissue sampling apparatus as recited in claim 1, wherein said apparatus is adapted to enter solid tissue, thereby creating a blind hole as it is advanced into said tissue.

26. The tissue sampling apparatus as recited in claim 1, wherein the tubular body is flexible and steerable in order to obtain tissue samples from any desired location on the wall of a tissue cavity, and the apparatus is adapted for delivery to a desired tissue location percutaneously.

27. The tissue sampling apparatus as recited in claim 26, and further comprising a percutaneous biopsy instrument having a hollow outer piercing needle which is adapted for entry into a patient's body, the hollow outer piercing needle including a lumen extending along its length, wherein the flexible tubular body is adapted for insertion into the patient's body through said hollow outer piercing needle lumen.

28. The tissue sampling apparatus as recited in claim 1, and further comprising a coating on the interior surface of the tubular body to facilitate transport of tissue samples therethrough.

29. The tissue sampling apparatus as recited in claim 1, and further comprising depth marks on said tubular body to facilitate positioning of the apparatus in a patient's body.

30. The tissue sampling apparatus as recited in claim 1, wherein said tubular body is adapted to accommodate insertion of a sensing probe through the primary lumen thereof.

31. The tissue sampling apparatus as recited in claim 30, wherein said sensing probe comprises a radiation detecting probe.

32. The tissue sampling apparatus as recited in claim 30, wherein said sensing probe comprises an ultrasound probe.

33. The tissue sampling apparatus as recited in claim 30, wherein said sensing probe comprises a multivision probe.

34. The tissue sampling apparatus as recited in claim 30, wherein said apparatus is adapted to accommodate a scissors through the primary lumen after the sensing probe has been removed therefrom, said scissors functioning to dissect distally to a position just proximal to a lesion of interest.

35. A tissue sampling apparatus, comprising:
    a tubular body having a primary lumen for receiving a tissue sample, the tubular body having a distal end, a proximal end, and a longitudinal axis;
    an electrosurgical wire disposed at the distal end of the tubular body, said wire comprising a single wire loop which is actuatable from a rest position to a severing position, the wire loop forming a semicircular cutting element disposed along a circumferential portion of the distal end of the tubular body in the rest position, and the wire being movable across a cross-sectional area of the distal end of the tubular body while being electrically energized, from the rest position to the severing position, wherein said wire lies along a circumferential portion of the distal end of the tubular body which is opposed to the circumferential portion along which the wire is disposed in the rest position, the wire having a pair of ends which are each fixedly attached to opposing sides of the tubular body distal end, the transverse movement of the wire across said cross-sectional area of the distal end of the tube from the rest position to the severing position functioning to sever a distal end of the tissue sample.

36. A tissue sampling apparatus, comprising:
    a tubular body having a primary lumen for receiving a tissue sample, the tubular body having a wall, distal end, a proximal end, and a longitudinal axis;
    a slit extending part of the way through the thickness of the tube wall, the slit creating a flexible band of material between the slit and the distal end of the tubular body, the flexible band of material being predisposed to rest in a partially collapsed position across the cross-sectional area of the tubular body;
    an inner coaxial tube insertable into the lumen of the tubular body to thereby push the material band into a circumferential configuration substantially coincident with the remainder of the tubular body, the tubular body being electrically conductive to conduct electrical energy from an electrocautery generator to the flexible band of material;
    said flexible band of material comprising an electrosurgical element, wherein when the inner coaxial tube is removed from the tubular body lumen, the electrically energized flexible band of material collapses to its rest position across the cross-sectional area of the tubular body, the collapsing motion of the band of material functioning to sever the distal end of a tissue sample.

37. A method of capturing a body tissue sample using a tissue sampling apparatus comprising a tubular body having a lumen extending therethrough, a distal end, at least one electrosurgical cutting element disposed distally of the distal end of the tubular body, an actuator for moving the at least one cutting element, and an electrocautery generator, the method comprising:
    activating the electrocautery generator to energize the at least one electrosurgical cutting element;
    advancing the tubular body through a solid tissue portion a desired distance so that one of the at least one energized electrosurgical cutting elements cuts a tissue sample core as the tissue sample enters the lumen, the cutting process creating a blind hole in said solid tissue portion; and
    actuating one of the at least one electrosurgical cutting elements so that it moves across at least a portion of a cross-sectional area of the tissue sample core at its distal end, thereby severing the distal end to capture the tissue sample core in a substantially intact condition within the tubular body lumen.

38. The method of capturing a body tissue sample as recited in claim 37, wherein the tissue sample core has a diameter substantially equal to an inner diameter of the tubular body.

39. The method of capturing a body tissue sample as recited in claim 37, wherein the at least one electrosurgical cutting element comprises only a single electrosurgical cutting element.

40. The method of capturing a body tissue sample as recited in claim 37, wherein the at least one electrosurgical cutting element comprises first and second electrosurgical cutting elements, the first electrosurgical cutting element cutting said tissue sample core during the advancing step, and the second electrosurgical cutting element severing a distal end of the tissue sample core during the actuating step.

* * * * *

UNITED STATES PATENT AND TRADEMARK OFFICE
CERTIFICATE OF CORRECTION

PATENT NO.    : 5,810,806
DATED         : September 22, 1998
INVENTOR(S)   : Mark A. Ritchart, Minh Tran, Mark Cole and Fred H. Burbank It is certified that error appears in the above-identified patent and that said Letters Patent is hereby corrected as shown below:

Column 3,
Line 51, "band-aid" should read -- BAND-AID® Brand Adhesive Bandage --.

Signed and Sealed this

Twenty-first Day of May, 2002

*Attest:*

*Attesting Officer*

JAMES E. ROGAN
*Director of the United States Patent and Trademark Office*